(12) United States Patent
Meyer et al.

(10) Patent No.: US 7,850,541 B2
(45) Date of Patent: *Dec. 14, 2010

(54) COMPOSITE METAL WOOD CLUB

(75) Inventors: Jeffrey W. Meyer, Fallbrook, CA (US); Scott A. Rice, San Diego, CA (US); Raymond L. Poynor, Oceanside, CA (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/469,034

(22) Filed: May 20, 2009

(65) Prior Publication Data

US 2009/0227389 A1 Sep. 10, 2009

Related U.S. Application Data

(60) Continuation of application No. 12/243,374, filed on Oct. 1, 2008, now Pat. No. 7,553,242, which is a continuation of application No. 11/938,883, filed on Nov. 13, 2007, now Pat. No. 7,431,664, which is a continuation of application No. 11/510,791, filed on Aug. 25, 2006, now Pat. No. 7,297,072, which is a division of application No. 10/799,118, filed on Mar. 12, 2004, now Pat. No. 7,214,142, which is a continuation-in-part of application No. 10/428,061, filed on May 1, 2003, now Pat. No. 7,029,403, which is a continuation-in-part of application No. 09/551,771, filed on Apr. 18, 2000, now Pat. No. 6,605,007.

(51) Int. Cl.
*A63B 53/00* (2006.01)
*A63B 53/04* (2006.01)

(52) U.S. Cl. .................. 473/314; 473/329; 473/332; 473/345; 473/349

(58) Field of Classification Search ......... 473/324–350, 473/287–292, 314
See application file for complete search history.

(56) References Cited

U.S. PATENT DOCUMENTS

| | | | |
|---|---|---|---|
| 1,318,325 A | 10/1919 | Klin | |
| 1,319,233 A | 10/1919 | Mattern | |

(Continued)

FOREIGN PATENT DOCUMENTS

CN 1114911 1/1996

(Continued)

OTHER PUBLICATIONS

Golf Digest, Sep. 1982, p. 25.

(Continued)

*Primary Examiner*—Sebastiano Passaniti
(74) *Attorney, Agent, or Firm*—Randy K. Chang

(57) ABSTRACT

A metal wood golf club head adapted for attachment to a shaft, comprising of a body portion and a crown portion, each portion constructed of a different density material. Combining a high-density material in the body portion, with a low-density material in the crown portion, creates an ultra-low center of gravity relative to the geometric face center, resulting in higher launch angles and spin rate ratios. The material for the crown portion is preferably a composite. A vibration dampening gasket is disposed between the ledge and lip sections of the body and crown respectively.

20 Claims, 11 Drawing Sheets

U.S. PATENT DOCUMENTS

| | | |
|---|---|---|
| 1,437,463 A | 12/1922 | Boye |
| 1,467,435 A | 9/1923 | Kinnear |
| 1,525,352 A | 2/1925 | Aitken |
| 1,543,691 A | 6/1925 | Beat |
| 1,582,836 A | 4/1926 | Link |
| 1,589,363 A | 6/1926 | Butchart |
| 1,595,589 A | 8/1926 | Tyler |
| 1,605,551 A | 11/1926 | Mattern |
| 1,699,874 A | 1/1929 | Buhrke |
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |
| 3,567,228 A | 3/1971 | Lynn |
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,021,047 A | 5/1977 | Mader |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,432,549 A | 2/1984 | Zebelean |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,303,922 A | 4/1994 | Lo |
| 5,318,300 A | 6/1994 | Schmidt et al. |
| 5,328,184 A | 7/1994 | Antonious |
| 5,333,872 A * | 8/1994 | Manning et al. ............ 473/291 |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,366,223 A | 11/1994 | Werner et al. |
| 5,380,010 A | 1/1995 | Werner et al. |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,423,546 A * | 6/1995 | Manning et al. ............ 473/331 |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,509,660 A | 4/1996 | Elmer |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,586,947 A * | 12/1996 | Hutin ........................ 473/324 |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |

| | | | |
|---|---|---|---|
| 5,743,813 A | 4/1998 | Chen et al. | |
| 5,753,170 A | 5/1998 | Muang | |
| 5,755,624 A | 5/1998 | Helmstetter | |
| 5,755,627 A | 5/1998 | Yamazaki et al. | |
| 5,762,567 A | 6/1998 | Antonious | |
| 5,766,092 A | 6/1998 | Mimeur et al. | |
| 5,766,094 A | 6/1998 | Mahaffey et al. | |
| 5,766,095 A | 6/1998 | Antonious | |
| 5,776,011 A | 7/1998 | Su et al. | |
| 5,807,190 A | 9/1998 | Krumme et al. | |
| 5,827,132 A | 10/1998 | Bamber | |
| RE35,955 E | 11/1998 | Lu | |
| D401,652 S | 11/1998 | Burrows | |
| 5,830,084 A | 11/1998 | Kosmatka | |
| 5,839,975 A | 11/1998 | Lundberg | |
| 5,842,934 A | 12/1998 | Ezaki et al. | |
| 5,851,159 A | 12/1998 | Burrows | |
| 5,851,160 A | 12/1998 | Rugge et al. | |
| 5,863,261 A | 1/1999 | Eggiman | |
| 5,873,791 A | 2/1999 | Allen | |
| 5,873,795 A | 2/1999 | Wozny et al. | |
| D406,294 S | 3/1999 | Burrows | |
| 5,888,148 A | 3/1999 | Allen | |
| 5,890,973 A | 4/1999 | Gamble | |
| D411,272 S | 6/1999 | Burrows | |
| 5,908,357 A | 6/1999 | Hsieh | |
| 5,921,872 A | 7/1999 | Kobayashi | |
| 5,931,746 A | 8/1999 | Soong | |
| 5,935,019 A | 8/1999 | Yamamoto | |
| 5,938,541 A | 8/1999 | Allen et al. | |
| 5,941,782 A | 8/1999 | Cook | |
| 5,944,619 A | 8/1999 | Cameron | |
| 5,954,596 A | 9/1999 | Noble et al. | |
| D415,807 S | 10/1999 | Werner et al. | |
| 5,961,394 A | 10/1999 | Minabe | |
| 5,967,905 A | 10/1999 | Nakahara et al. | |
| 5,971,868 A | 10/1999 | Kosmatka | |
| 5,993,329 A | 11/1999 | Shich | |
| 6,007,432 A | 12/1999 | Kosmatka | |
| 6,027,416 A | 2/2000 | Schmidt et al. | |
| 6,139,445 A | 10/2000 | Werner et al. | |
| 6,143,169 A | 11/2000 | Lee | |
| 6,152,833 A | 11/2000 | Werner et al. | |
| 6,248,025 B1 | 6/2001 | Murphy | |
| 6,319,150 B1 | 11/2001 | Werner et al. | |
| 6,338,683 B1 | 1/2002 | Kosmatka | |
| 6,354,962 B1 * | 3/2002 | Galloway et al. | 473/342 |
| 6,368,234 B1 | 4/2002 | Galloway | |
| 6,381,828 B1 | 5/2002 | Boyce | |
| 6,390,933 B1 | 5/2002 | Galloway et al. | |
| 6,398,666 B1 | 6/2002 | Evans et al. | |
| 6,435,982 B1 | 8/2002 | Galloway et al. | |
| 6,478,693 B2 * | 11/2002 | Matsunaga et al. | 473/345 |
| 6,506,129 B2 | 1/2003 | Chen | |
| 6,605,007 B1 * | 8/2003 | Bissonnette et al. | 473/329 |
| 6,626,769 B1 | 9/2003 | Lin | |
| 6,648,774 B1 | 11/2003 | Lee | |
| 6,663,501 B2 | 12/2003 | Chen | |
| 6,669,576 B1 | 12/2003 | Rice | |
| 6,755,627 B2 | 6/2004 | Chang | |
| 6,776,726 B2 | 8/2004 | Sano | |
| 6,800,038 B2 * | 10/2004 | Willett et al. | 473/329 |
| 6,899,638 B2 * | 5/2005 | Iwata et al. | 473/329 |
| 6,994,636 B2 | 2/2006 | Hocknell et al. | |
| 7,029,403 B2 | 4/2006 | Rice et al. | |
| 7,041,003 B2 * | 5/2006 | Bissonnette et al. | 473/329 |
| 7,066,832 B2 * | 6/2006 | Willett et al. | 473/329 |
| 7,137,906 B2 | 11/2006 | Tsunoda et al. | |
| 7,140,975 B2 * | 11/2006 | Bissonnette et al. | 473/329 |
| 7,169,059 B2 * | 1/2007 | Rice et al. | 473/329 |
| 7,207,898 B2 * | 4/2007 | Rice et al. | 473/329 |
| 7,211,006 B2 | 5/2007 | Chang | |
| 7,214,142 B2 | 5/2007 | Meyer et al. | |
| 7,220,190 B2 * | 5/2007 | Hirano | 473/342 |
| 7,261,643 B2 * | 8/2007 | Rice et al. | 473/329 |
| 7,297,072 B2 | 11/2007 | Meyer et al. | |
| 7,331,877 B2 * | 2/2008 | Yamaguchi et al. | 473/329 |
| 7,338,388 B2 * | 3/2008 | Schweigert et al. | 473/342 |
| 7,361,099 B2 * | 4/2008 | Rice et al. | 473/329 |
| 7,422,527 B2 * | 9/2008 | Rice et al. | 473/329 |
| 7,431,664 B2 | 10/2008 | Meyer et al. | |
| 7,520,819 B2 * | 4/2009 | Rice et al. | 473/329 |
| 7,537,528 B2 * | 5/2009 | Rice et al. | 473/329 |
| 7,549,934 B2 * | 6/2009 | Rice | 473/329 |
| 7,553,242 B2 * | 6/2009 | Meyer et al. | 473/314 |
| 7,584,531 B2 * | 9/2009 | Schweigert et al. | 29/557 |
| 2001/0012804 A1 * | 8/2001 | Matsunaga et al. | 473/345 |
| 2003/0064823 A1 * | 4/2003 | Yamamoto | 473/329 |
| 2004/0048681 A1 | 3/2004 | Nishio | |
| 2004/0157678 A1 | 8/2004 | Kohno | |
| 2004/0266548 A1 | 12/2004 | Cheng et al. | |
| 2005/0209019 A1 * | 9/2005 | Schweigert | 473/329 |
| 2006/0111198 A1 * | 5/2006 | Matsunaga | 473/329 |

FOREIGN PATENT DOCUMENTS

| | | |
|---|---|---|
| GB | 2268693 A | 1/1994 |
| GB | 2331938 A | 6/1999 |
| JP | 59207169 | 11/1984 |
| JP | 61033682 | 2/1986 |
| JP | 61162967 | 7/1986 |
| JP | 61181477 | 8/1986 |
| JP | 61185281 | 8/1986 |
| JP | 61240977 | 10/1986 |
| JP | 1244770 | 9/1989 |
| JP | 02130519 | 5/1990 |
| JP | 4020357 | 1/1992 |
| JP | 4327864 | 11/1992 |
| JP | 5212526 | 8/1993 |
| JP | 05237207 | 9/1993 |
| JP | 6007487 | 1/1994 |
| JP | 06031016 | 2/1994 |
| JP | 6114126 | 4/1994 |
| JP | 6126002 | 5/1994 |
| JP | 6154367 | 6/1994 |
| JP | 6182005 | 7/1994 |
| JP | 6269518 | 9/1994 |
| JP | 8168541 | 7/1996 |
| JP | 8243194 | 9/1996 |
| JP | 8280853 | 10/1996 |
| JP | 8280854 | 10/1996 |
| JP | 8294550 | 11/1996 |
| JP | 9028842 | 2/1997 |
| JP | 9047531 | 2/1997 |
| JP | 9154985 | 6/1997 |
| JP | 9168613 | 6/1997 |
| JP | 9192270 | 7/1997 |
| JP | 9192273 | 7/1997 |
| JP | 9239074 | 9/1997 |
| JP | 9239075 | 9/1997 |
| JP | 9248353 | 9/1997 |
| JP | 2717759 | 11/1997 |
| JP | 9294833 | 11/1997 |
| JP | 9299519 | 11/1997 |
| JP | 10024126 | 1/1998 |
| JP | 10024128 | 1/1998 |
| JP | 10085369 | 4/1998 |
| JP | 10118227 | 5/1998 |
| JP | 10137372 | 5/1998 |
| JP | 10155943 | 6/1998 |
| JP | 10258142 | 9/1998 |
| JP | 10263121 | 10/1998 |
| JP | 10323410 | 12/1998 |

| | | |
|---|---|---|
| JP | 10337347 | 12/1998 |

OTHER PUBLICATIONS

Golf Digest, Dec. 1981, p. 58-59.

"Variable Face Thickness Technology," Calloway Golf advertisement, undated.

* cited by examiner

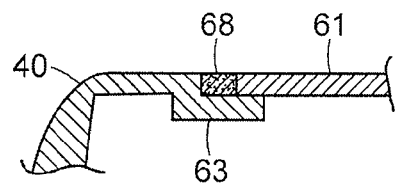
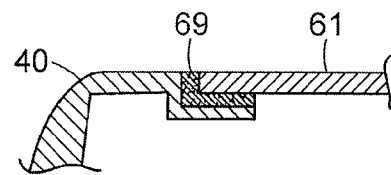
FIG. 12g
FIG. 12h
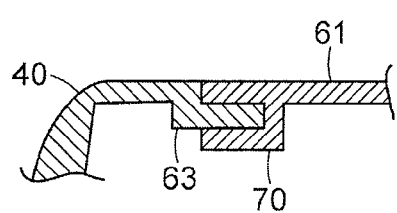
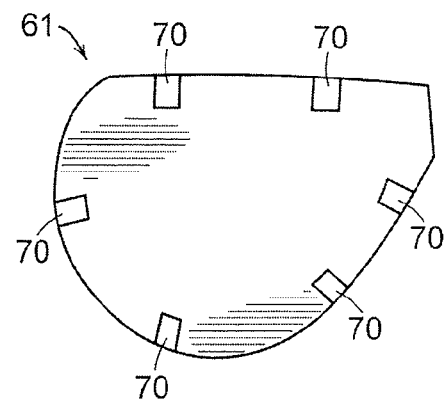
FIG. 12i
FIG. 12j

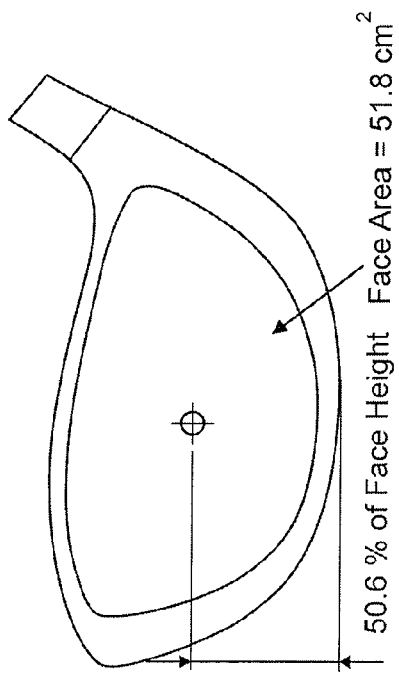
FIG. 13
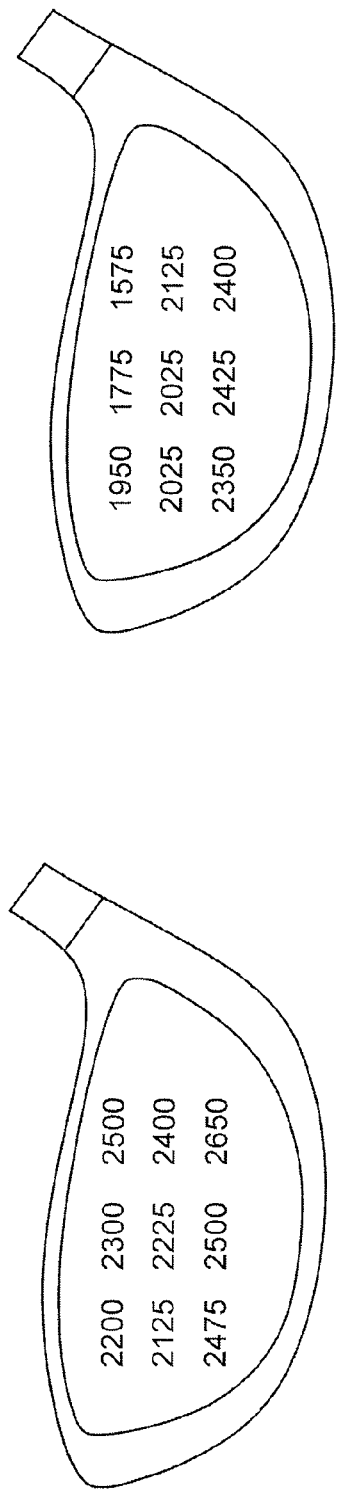
FIG. 14a
King Cobra 454 COMP
Spin Range Variance: 475 rpm
Average Spin: 2375
Effective Hitting Area: 7.5 in²
FIG. 14b
Callaway ERC Fusion
Spin Range Variance: 850 rpm
Average Spin: 2070
Effective Hitting Area: 5.0 in²

COMPOSITE METAL WOOD CLUB

CROSS-REFERENCE TO RELATED APPLICATION

The present application is a continuation of U.S. patent application Ser. No. 12/243,374, filed on Oct. 1, 2008, now U.S. Pat. No. 7,553,242 which is a continuation of U.S. patent application Ser. No. 11/938,883, filed on Nov. 13, 2007, now U.S. Pat. No. 7,431,664, which is a continuation of U.S. patent application Ser. No. 11/510,791, filed on Aug. 25, 2006, now U.S. Pat. No. 7,297,072, which is a divisional of U.S. patent application Ser. No. 10/799,118, filed on Mar. 12, 2004, now U.S. Pat. No. 7,214,142, which is a continuation-in-part of U.S. patent application Ser. No. 10/428,061, filed on May 1, 2003, now U.S. Pat. No. 7,029,403, which is a continuation-in-part of U.S. patent application Ser. No. 09/551,771, filed on Apr. 18, 2000, now U.S. Pat. No. 6,605,007. The disclosures of all the parent patent applications are incorporated herein in their entirety.

FIELD OF THE INVENTION

The present invention relates to an improved golf club head. More particularly, the present invention relates to a golf club head with an improved striking face and improved shock absorption between the mating portions making up the body of the club head.

BACKGROUND

The complexities of golf club design are well known. The specifications for each component of the club (i.e., the club head, shaft, hosel, grip, and sub-components thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, face progression, face size, sole curvature, center of gravity, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the face or body of the club head, and fillers within hollow club heads.

Golf club heads must also be strong to withstand the repeated impacts that occur during collisions between the golf club and the golf ball. The loading that occurs during this transient event can accelerate the golf ball to several orders of magnitude greater than gravity. Thus, the club face and body should be designed to resist permanent deformation or catastrophic failure by material yield or fracture. Conventional hollow metal wood drivers made from titanium typically have a uniform face thickness exceeding 0.10 inch to ensure structural integrity of the club head.

Players generally seek a metal wood driver and golf ball combination that delivers maximum distance and landing accuracy. The distance a ball travels after impact may be dictated by variables including: the magnitude and direction of the ball's translational velocity; and, the ball's rotational velocity or spin. Environmental conditions, including atmospheric pressure, humidity, temperature, and wind speed, further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

The United States Golf Association (USGA), the governing body for the rules of golf in the United States, has specifications for the performance of golf balls. These performance specifications dictate the size and weight of a conforming golf ball. One USGA rule limits the golf ball's initial velocity after a prescribed impact to 250 feet per second ±2% (or 255 feet per second maximum initial velocity). To achieve greater golf ball travel distance, ball velocity after impact and the coefficient of restitution of the ball-club impact must be maximized while remaining within this rule.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation must be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the allowable deformation of the club face, including uniform face thinning, thinned faces with ribbed stiffeners and varying thickness, among others. These designs should have sufficient structural integrity to withstand repeated impacts without permanent deformation of the club face. In general, conventional club heads also exhibit wide variations in the coefficient of restitution depending on the impact location on the face of the club. Furthermore, the accuracy of conventional clubs is highly dependent on impact location.

It has been reported in F. Werner and R. Greig, "How Golf Clubs Really Works and How to Optimize Their Designs", Ch. 4, pp. 17-21 (2000) that a typical distribution of golf ball hits on the face of a driver club follows an elliptical pattern with its major axis orientating in a direction from high toe to low heel. The size of the hit distribution depends on the handicap of the golfer. Players with low handicap have smaller elliptical distribution and players with high handicap have larger elliptical distribution. These authors also patented golf clubs that have an elliptical outer hitting face that aligns in the direction of high toe to low heel. See U.S. Pat. No. 5,366,233, entitled "Golf Club Face for Drivers," issued on Nov. 22, 1994. However, there is no teaching to align the coefficient of restitution of the golf club head to the ball impact pattern.

SUMMARY OF THE INVENTION

The present invention relates to a golf club head adapted for attachment to a shaft. The head includes a hitting face and a body. The hitting face is configured and dimensioned so that it includes at least an inner zone and a concentric intermediate zone. The inner zone has relatively high flexural stiffness and the intermediate zone has lower flexural stiffness. Preferably, the inner zone has a shape that comprises a major axis and a minor axis and the major axis aligns substantially in the direction of high heel to low toe. The inner zone can have an elliptical shape or a substantially parallelogram shape. The inner zone and intermediate zone may have same shape or different shape.

This arrangement of inner and intermediate zones forms an area of relatively high flexural stiffness in the direction of high heel to low toe, thereby creating high resilience in the direction of high toe to low heel. In other words, this arrangement creates a gradient of flexural stiffness in the direction of high toe to low heel, and produces a desirable effect of manipulating resilience or higher coefficient of restitution (COR) in that direction. This area of improved coefficient of restitution advantageously coincides with the ball impact pattern that golfers typically make on the hitting face.

The inventive club head encompasses a measurement zone that exhibits high COR where the lowest COR is at least 93% of the peak COR within this measurement zone. The measurement zone is defined by a rectangle having the dimensions of 0.5 inch by 1.0 inch, and the COR values are measured at the corners of the rectangle, the mid-points of the sides and the geometric center of the rectangle. The geometric center of the measurement zone preferably coincides with the geometric center of the face of the club.

The above is accomplished by providing the inner zone with a first flexural stiffness and the intermediate zone with a second flexural stiffness. Flexural stiffness is defined as Young's modulus or elastic modulus (E) times the zone's thickness (t) cubed or $Et^3$. The first flexural stiffness is substantially higher than the second flexural stiffness. As a result, upon ball impact, the intermediate zone exhibits substantial elastic deformation to propel the ball.

In one embodiment, the first flexural stiffness is at least three times the second flexural stiffness. In other embodiments, the first flexural stiffness is six to twelve times the second flexural stiffness. More preferably, the first flexural stiffness is greater than 25,000 lb-in. Most preferably, the first flexural stiffness is greater than 55,000 lb-in. Preferably, the second flexural stiffness is less than 16,000 lb-in. More preferably, the second flexural stiffness is less than 10,000 lb-in.

Since the flexural stiffness is a function of material properties and thickness, the following techniques can be used to achieve the substantial difference between the first and second flexural stiffness: 1) different materials can be used for each portion, 2) different thicknesses can be used for each portion, or 3) different materials and thicknesses can be used for each portion.

The golf club head may further include a perimeter zone disposed between the intermediate zone and the body of the club. In one embodiment, the perimeter zone has a third flexural stiffness that is at least two times greater than the second flexural stiffness In the club heads discussed above, the inner, intermediate and optional perimeter zones can have any shape that has a major axis and a minor axis, such as elliptical, rhombus, diamond, other quadrilateral shapes with one or more rounded corners and the like. The zones may also have a substantially parallelogram shape. Furthermore, the club head inner cavities can have a volume greater than about 100 cubic centimeters, and more preferably a volume greater than about 300 cubic centimeters. In other words, the club head in accordance to the present invention can be used in driver clubs and/or fairway clubs. In addition, the inner, intermediate, and perimeter zones can each have variable thickness.

Another feature of the present invention is locating the center of gravity of the club head with respect to a Cartesian coordinate system. The origin of the Cartesian coordinate system preferably coincides with the geometric center of the hitting face. The X-axis is a horizontal axis positioned tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club. The center of gravity is preferably located behind and lower than the geometric center of the face.

In one preferred embodiment, the center of gravity is spaced from the geometric center along the Z-axis by about −0.050 inch to about −0.150 inch, and more preferably by about −0.110 inch. The center of gravity is preferably spaced about ±0.050 inch, and more preferably about +0.015 inch from the geometric center along the X-axis. The center of gravity is preferably spaced about +2.0 inches and more preferably about +1.35 inches from the geometric center along the Y-axis.

The hitting face may comprise a face insert and a face support. The face support defines a cavity adapted to receive the face insert. The hitting face may further comprise at least one side wall, which can be a partial crown portion or a partial sole portion. Preferably, the inner zone is located on the face insert, and the intermediate zone may partially be located on the face insert and partially on the face support.

Another aspect of the invention provides for a crown portion to be composed of a material having a lower density than a body portion. The material for the crown portion selected from such materials as composite, thermoplastic or magnesium, and preferably graphite composite. The crown portion having an inner surface layer integrally composed of a vibration dampening or acoustical attenuating material. One embodiment would include a titanium mesh material.

An embodiment of the invention includes a non-integral dampening material, juxtaposed between the body and crown portions.

A preferred embodiment would be a gasket juxtaposed between the body and the crown portions Yet still another embodiment of the invention is comprised of a body and light weight crown with a vibration dampening gap there between. The gap is preferably filled with putty or other shock absorption material such as a rubber based structural adhesive.

BRIEF DESCRIPTION OF THE DRAWINGS

Preferred features of the present invention are disclosed in the accompanying drawings, wherein similar reference characters denote similar elements throughout the several views, and wherein:

FIG. 12g is a cross-section view of an embodiment of the invention having a gap filled with a shock absorption material between the crown portion and lip section;

FIG. 12h is a cross-section view of an embodiment of the invention having an "L" shaped gasket composed of a shock absorption material between the crown portion and lip section;

FIG. 12i is a cross-section view of an embodiment of the invention having a "Y" joint on the crown portion;

FIG. 12j is a plan view of the inner side of the crown portion showing the plurality of "Y" joints about the perimeter;

FIG. 13 is a schematic of the front face of an embodiment of the invention depicting the location of the center of gravity;

FIG. 14a is a front schematic depicting a 9 point spin variance across the front face of an embodiment of the invention; and FIG. 14b is a front schematic depicting a 9 point spin variance across the front face of a prior art club head.

DETAILED DESCRIPTION OF THE PREFERRED EMBODIMENT

Figure 5:
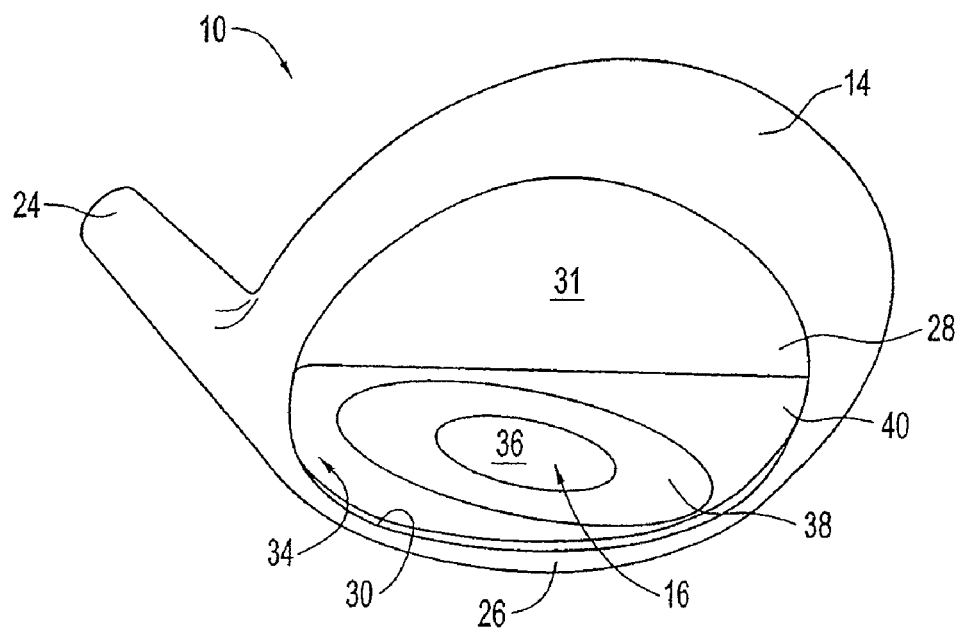
FIG. 5 is a bottom, perspective view of the golf club head of FIG. 1.

Referring to FIGS. 1-5, a first embodiment of a golf club head 10 of the present invention is shown. Club head 10 includes shell 12 with body 14, hitting face 16, toe portion 18, heel portion 20, sole plate 22, hosel 24, bottom portion 26, crown portion 28, and rear portion 29. The sole plate 22 fits in a recess 30 (as shown in FIG. 5) in the bottom portion 26 of body 14. The shell 12 and sole plate 22 create an inner cavity 31 (as shown in FIG. 5). The hitting face 16 has an exterior surface 32 and an interior surface 34. The exterior surface 32 is generally smooth except for external grooves (which are omitted for clarity). Preferably, interior surface 34 has elevated or depressed areas to accommodate the varying thickness of hitting face, as discussed below and shown in FIGS. 3A-3D.

A golf club shaft (not shown) is attached at hosel 24 and is disposed along a shaft axis SHA. The hosel may extend to the bottom of the club head or may terminate at a location between the top and bottom portions of the head. The hosel can also terminate flush with the top portion or extend into the cavity within the head.

Inner cavity 31 of club head 10 may be empty, or alternatively may be filled with foam or other low specific gravity material. It is preferred that the inner cavity 31 has a volume greater than 100 cubic centimeters, and more preferably greater than 300 cubic centimeters. In other words, the club head design in accordance to the present invention can be used with any driver club, as well as any fairway club. Preferably, the mass of the inventive club head is greater than 150 grams but less than 250 grams.

Figure 1:
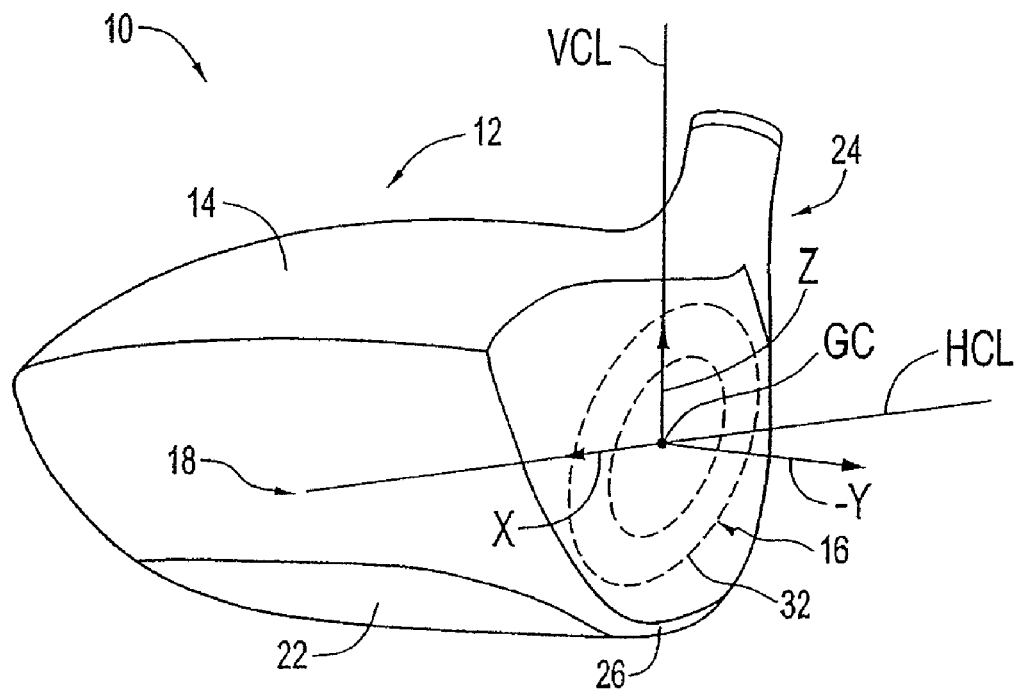
FIG. 1 is a toe side, front, perspective view of an embodiment of a golf club head of the present invention.
Figure 2:
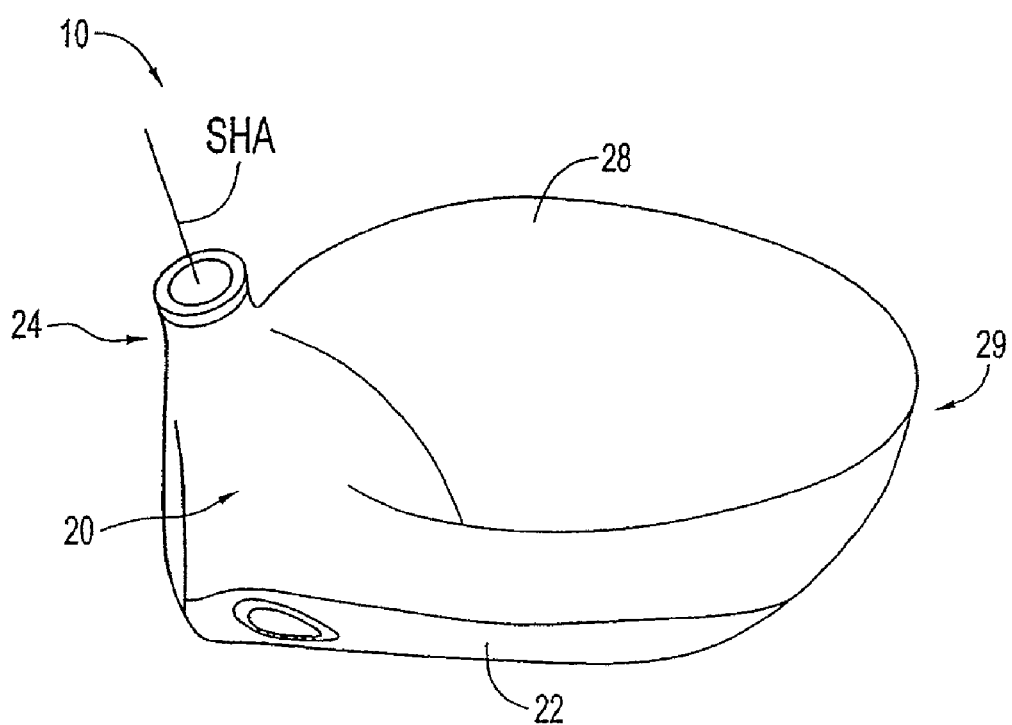
FIG. 2 is a heel side, rear, perspective view of the golf club head of FIG. 1.
Figure 3:
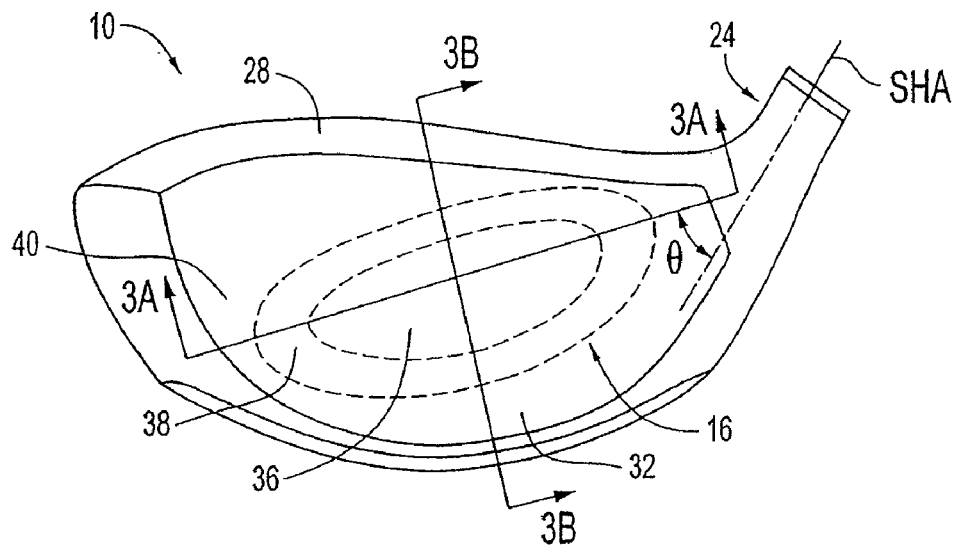
FIG. 3 is a front, elevational view of the golf club head of FIG. 1.
Figure 3A:
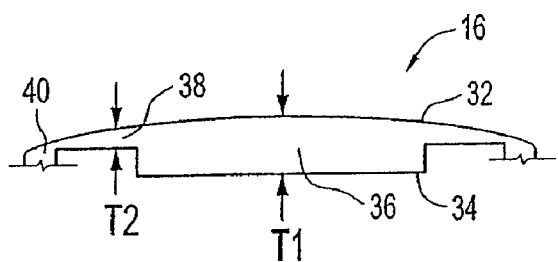
FIG. 3A is a cross-sectional view of the face of the golf club head of FIG. 1 along line 3A-3A.
Figure 3B:
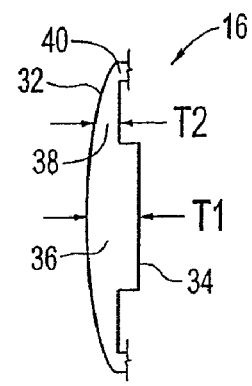
FIG. 3B shows a cross-sectional view the face of the golf club head of FIG. 1 along line 3B-3B.
Figure 3C:
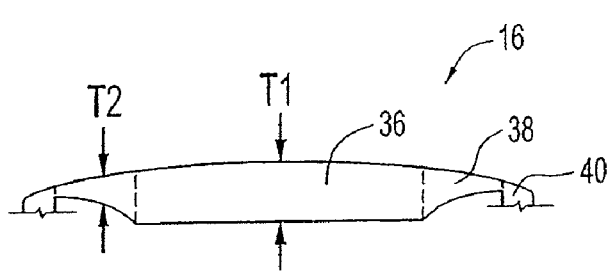
FIGS. 3C and 3D are alternative embodiments of FIGS. 3A and 3B, respectively.
Figure 3D:
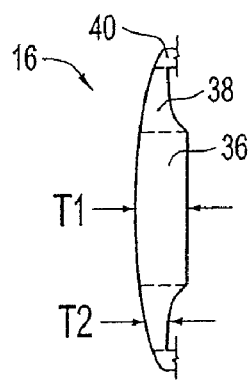
Figure 4:
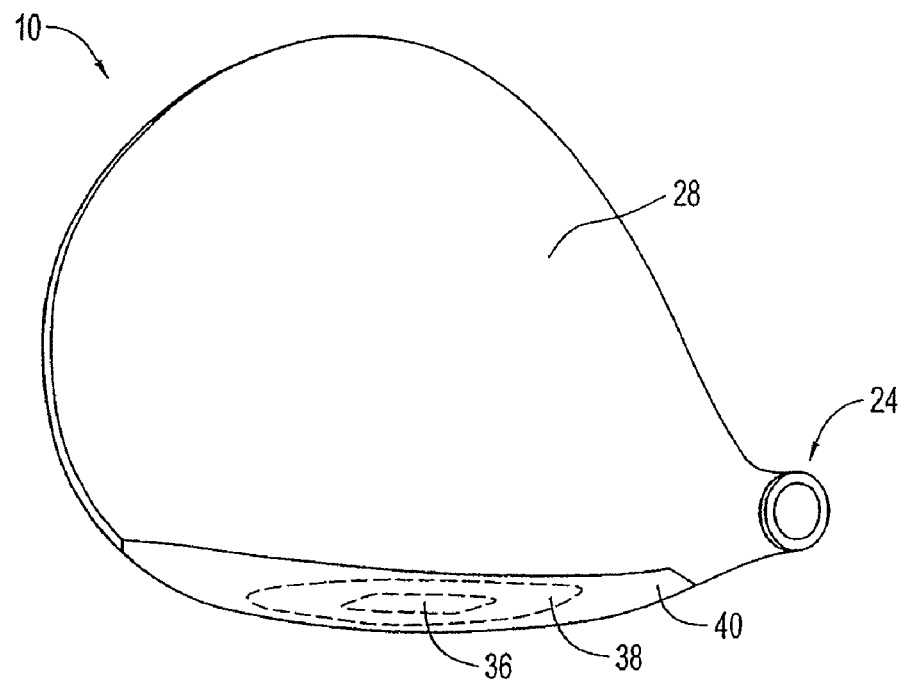
FIG. 4 is a top view of the golf club head of FIG. 1.

Referring to FIGS. 1 and 3-3D, the face 16 includes an inner zone or portion 36, an intermediate zone or surrounding portion 38 adjacent the inner zone 36, and an optional perimeter zone or outer portion 40. The intermediate zone 38 preferably surrounds inner zone 36, and the perimeter zone 40 preferably surrounds the intermediate zone 38. The inner zone 36 is a contiguous zone located on the hitting face 16 and contains a geometric center ("GC") of the hitting face. As shown, inner zone 36 and its concentric zones have a generally elliptical shape with a major axis in the direction of high heel to low toe. As used herein, the term "ellipse" or "elliptical" refers to non-circular shapes that have discernable major axis and minor axis, and include, but are not limited to, any quadrilateral shapes, geometrical ellipses, quadrilateral shapes with one or more rounded corner(s) and unsymmetrical elliptical shapes. Also, the term "concentric" refers to shapes that substantially encircle or surround other shapes. The "major axis" is defined as the axis coinciding with the longest length that can be drawn through the non-circular shapes without intersecting the perimeter of the shapes at more than two locations, i.e., at the start and end points of said length. The "minor axis" is orthogonal to the major axis at or near its midpoint.

The major axis of inner portion 36 forms an angle, θ, with the shaft axis, SHA. Preferably, angle θ is between about 10° to about 60°, more preferably between about 20° and about 50°, and most preferably between about 25° and about 45°. Additionally, the ratio of the length of the major axis to the length of minor axis is preferably greater than 1.0 and more preferably less than about 6.0.

Preferably, zones 36, 38 and 40 are concentric to each other within hitting face 16. The inner zone 36 has a first thickness $T_1$. The intermediate zone 38 has a second thickness $T_2$. The first thickness $T_1$ is greater than the second thickness $T_2$. Typically, when the club head is cast, the perimeter zone 40 is thicker than the intermediate zone 38. Alternatively, the hitting face may also be forged. However, the present invention is not limited to any manufacturing technique. $T_1$ may range from about 1.5 mm to about 7.5 mm and $T_2$ may range from about 0.8 mm to about 3.0 mm. Preferably, the first thickness $T_1$ is equal to about one and a half (1.5) times the thickness $T_2$ to about four (4) times the thickness $T_2$.

The thickness relationships between the zones 36, 38, and 40 are provided so that a predetermined relationship exists between flexural stiffness exhibited by each of the zones.

For clubs that have a hitting face made from a single material, such as titanium or titanium alloy, the area of highest thickness corresponds to the portion with the highest flexural stiffness. Flexural stiffness (FS) of each portion is defined as:

$$FS = E(t^3),$$

where:

E is the elastic modulus or Young's modulus of the material of the portion, and t is the thickness of the portion.

Young's modulus of titanium is about $16.5 \times 10^6$ lbs/in$^2$, and thickness is typically measured in inch. Hence, FS as used in this application has the unit of lb·in.

The inner zone 36 has a first flexural stiffness $FS_1$. The intermediate zone 38 has a second flexural stiffness $FS_2$. The perimeter zone 40 has a third flexural stiffness $FS_3$. The predetermined relationship between the portions is that the first flexural stiffness $FS_1$ is substantially greater than the second flexural stiffness $FS_2$, and the optional third flexural stiffness $FS_3$ is substantially greater than the second flexural stiffness $FS_2$. Preferably, the first flexural stiffness $FS_1$ is at least three times greater than the second flexural stiffness $FS_2$, i.e., $(FS_1/FS_2) \geq 3$. When the above ratio of flexural stiffness is less than three, the inner zone sustains excessive deformation during impact and accuracy of the club is diminished. More preferably, the first flexural stiffness $FS_1$ is about six (6) to twelve (12) times greater than the second flexural stiffness $FS_2$. Most preferably, the first flexural stiffness $FS_1$ is about eight (8) times greater than the second flexural stiffness $FS_2$. Preferably, the third flexural stiffness $FS_3$ is at least two times greater than the second flexural stiffness $FS_2$, i.e., $(FS_3/FS_2) \geq 2$.

Alternatively, the flexural stiffness, $FS_1$, $FS_2$ or $FS_3$, can be determined for two combined adjacent zones, so long as the preferred ratio $(FS_1/FS_2) \geq 3$ or $(FS_3/FS_2) \geq 2$ is satisfied. For example, $FS_1$, can be calculated to include both zones 36 and 38, and $FS_3$ can be calculated to include both zones 38 and 40.

The thickness of the zones, $T_1$ and $T_2$, may be constant within the zone as illustrated in FIGS. 3A and 3B, or may vary within the zone as illustrated in FIGS. 3C and 3D. For the purpose of determining FS, when the thickness varies, a weighted average thickness is calculated. The determination of FS when the thickness varies or when the material is anisotropic is fully discussed in the parent patent application, which has already been incorporated by reference in its entirety.

In club head 10 (as shown in FIGS. 3-3D), the above flexural stiffness relationships are achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the zones can be the same or different depending on the elastic modulus of the material of each zone. It is also possible to obtain the required flexural stiffness ratio through the use of structural ribs, reinforcing plates, and thickness parameters.

Quantitatively, it is preferred that the first flexural stiffness $FS_1$ is greater than 25,000 lb-in. When the first flexural stiffness is less than 25,000 lb-in excessive deformation of the inner region can occur during impact and accuracy is diminished. More preferably, the first flexural stiffness $FS_1$ is greater than 55,000 lb-in. Preferably, the second flexural stiffness $FS_2$ is less than 16,000 lb-in. When the second flexural stiffness is greater than 16,000 lb-in, the resultant ball velocity is reduced. More preferably, the second flexural stiffness $FS_2$ is less than 10,000 lb-in and, most preferably, less than 7,000 lb-in.

Referring to FIG. 3, it is preferred that inner zone 36 has an area that is between about 15% and about 60% of the exterior surface area 32. The percentage of face area is computed by dividing the area of each zone 36, 38, or 40 by the total face area of exterior surface 32. It should be noted that the face area of exterior surface 32 is equivalent to the total area of zones 36, 38, and 40. When the inner zone 36 is less than 15% of the total face area, then accuracy can be diminished. When inner portion 36 is greater than 60% of the face area 32, then the coefficient of restitution can be diminished.

Referring again to FIG. 1, the club head 10 is further formed so that a center of gravity of the club head has a predetermined relationship with respect to a Cartesian coordinate system with its center located on hitting face 16 and coincident with the geometric center GC of the face 16. The hitting face 16 includes a vertical centerline VCL and a horizontal centerline HCL perpendicular thereto. The geometric center (GC) of hitting face 16 is located at the intersection of centerlines VCL and HCL. The VCL and HCL are co-linear with the X-axis and the Z-axis of a Cartesian coordinate system, described below. Preferably, the GC of the inner zone 36 is spaced from the GC of hitting face 16 by a distance of less than about 0.10 inch, more preferably less than about 0.05 inch and most preferably less than about 0.025 inch. The GC of inner zone 36 may be coincident with the GC of hitting face 16. The GC of inner zone 36 can be defined as the intersection between the major axis and the minor axis of the zone.

The Cartesian coordinate system is defined as having the origin coincident with the geometric center of the hitting face. The hitting face is not a rectilinear plane, but due to the bulge and roll radii it is a curvilinear surface. The X-axis is a horizontal axis lying tangent to the geometric center of the hitting face with the positive direction toward the heel of the club. The Y-axis is another horizontal axis orthogonal to the X-axis with the positive direction toward the rear of the club. The Z-axis is a vertical axis orthogonal to both the X-axis and Y-axis with the positive direction toward the crown of the club.

The center of gravity is preferably located both behind and lower than the geometric center of the face, when the club head is resting on a flat surface (i.e., at its natural loft). In one preferred embodiment, the center of gravity of club head 10 is spaced from the geometric center along the Z-axis between about −0.050 inch and about −0.150 inch, more preferably about −0.110 inch. The center of gravity is preferably spaced about ±0.050 inch, more preferably about 0.015 inch, from the geometric center along the X-axis. The center of gravity is preferably spaced about 2.0 inches or less and more preferably about 1.35 inches or less from the geometric center along the Y-axis.

The center of gravity for the club head can be achieved by controlling the configuration and dimensions of the club head in addition to adding predetermined weights to the sole plate or to the club head. Other known methods of weight manipulation can be used to achieve the inventive center of gravity location as set forth above.

Figure 6:
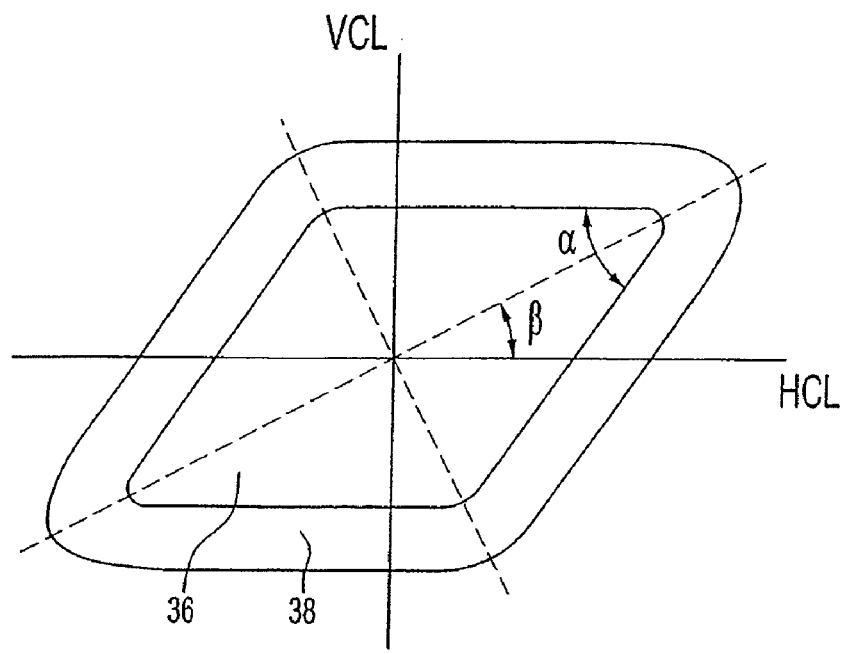
FIG. 6 is a schematic view of substantially parallelogram shaped the inner and intermediate zones.

FIG. 6 illustrates another embodiment of the present invention. Central zone 36 has a generally parallelogram shape, such that the opposite sides are generally parallel and the angles formed between adjacent sides are rounded. More specifically, the acute angle α of central zone 36 is preferably between 40° and 85°. Additionally, the major axis of central zone 36, as shown, forms an angle β with the HCL, which preferably is between 5° and 45°. The major axis is the line connecting the two acute angles of the parallelogram. Similar to the embodiments disclosed above, intermediate zone 38 surrounds central zone 36, and the relative thickness and ratio of FS between zone 36 and zone 38 follow the relationships discussed above.

Figure 7:
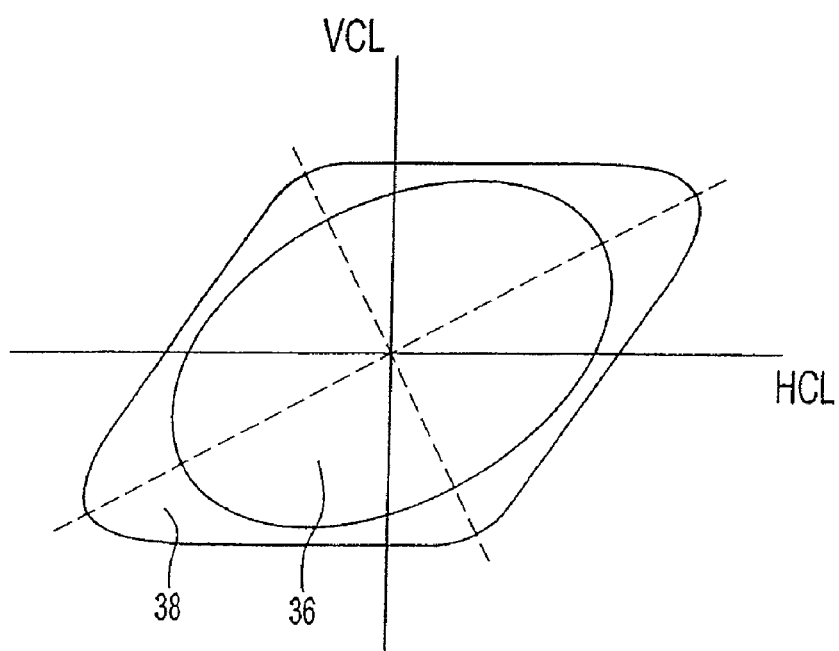
FIG. 7 is a schematic view of the inner and intermediate zones with substantially parallelogram and elliptical shape.

As shown in FIG. 7, central zone 36 can be an ellipse while intermediate zone 38 can have a generally parallelogram shape. Conversely, central zone 36 can have a generally parallelogram shape, while intermediate zone 38 can be an ellipse. Furthermore, as illustrated intermediate zone 38 may have varying width.

Figure 8:
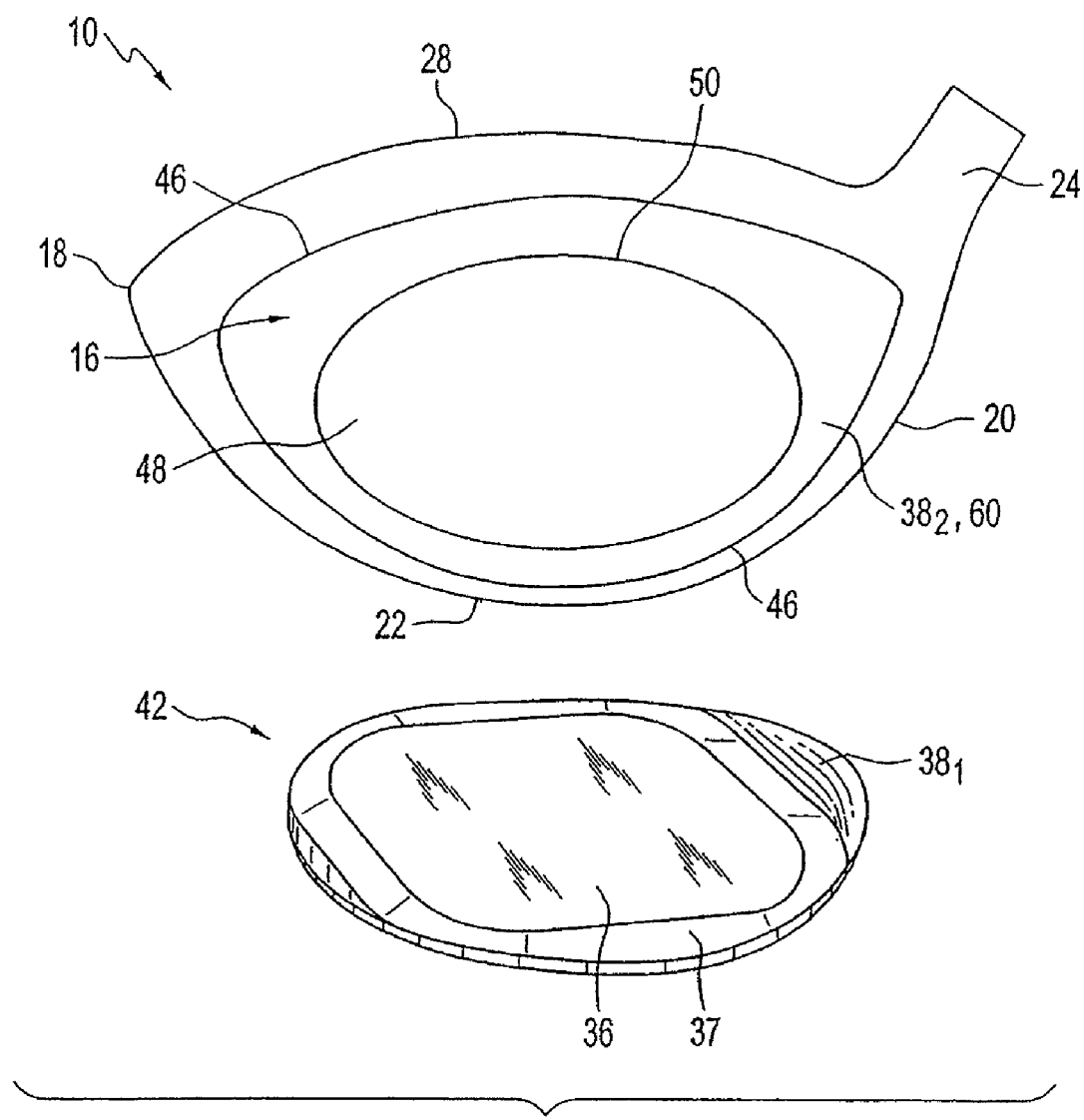
FIG. 8 is a front, exploded view of another embodiment of the present invention.

In accordance to another aspect of the present invention, hitting face 16 may comprise a face insert 42 and face support 44, as shown in FIG. 8. In this embodiment, hitting face 16 is delineated from crown 28, toe 18, sole 22 and heel 20 by parting line 46. Central zone 36 is preferably disposed on the back side of face insert 42, and, as shown, has a generally parallelogram shape. Intermediate zone 38, designated as $38_1$ and $38_2$, can be disposed partially on face insert 42 and partially on face support 44. A transition zone 37 having variable thickness is disposed between central zone 36 and intermediate zone 38. Preferably, the thickness of central zone 36 is reduced to the lesser thickness of intermediate zone 38 within transition zone 37. This reduces any local stress-strain caused by impacts with golf balls due to abrupt changes in thickness. Face support 44 defines hole 48, which is bordered by rim 50. Face insert 42 can be attached to face support 44 by welding at or around rim 50. For the purpose of determining the FS ratio for this embodiment, the $FS_1$ of the inner zone includes both zone 36 and zone 37.

Figure 9:
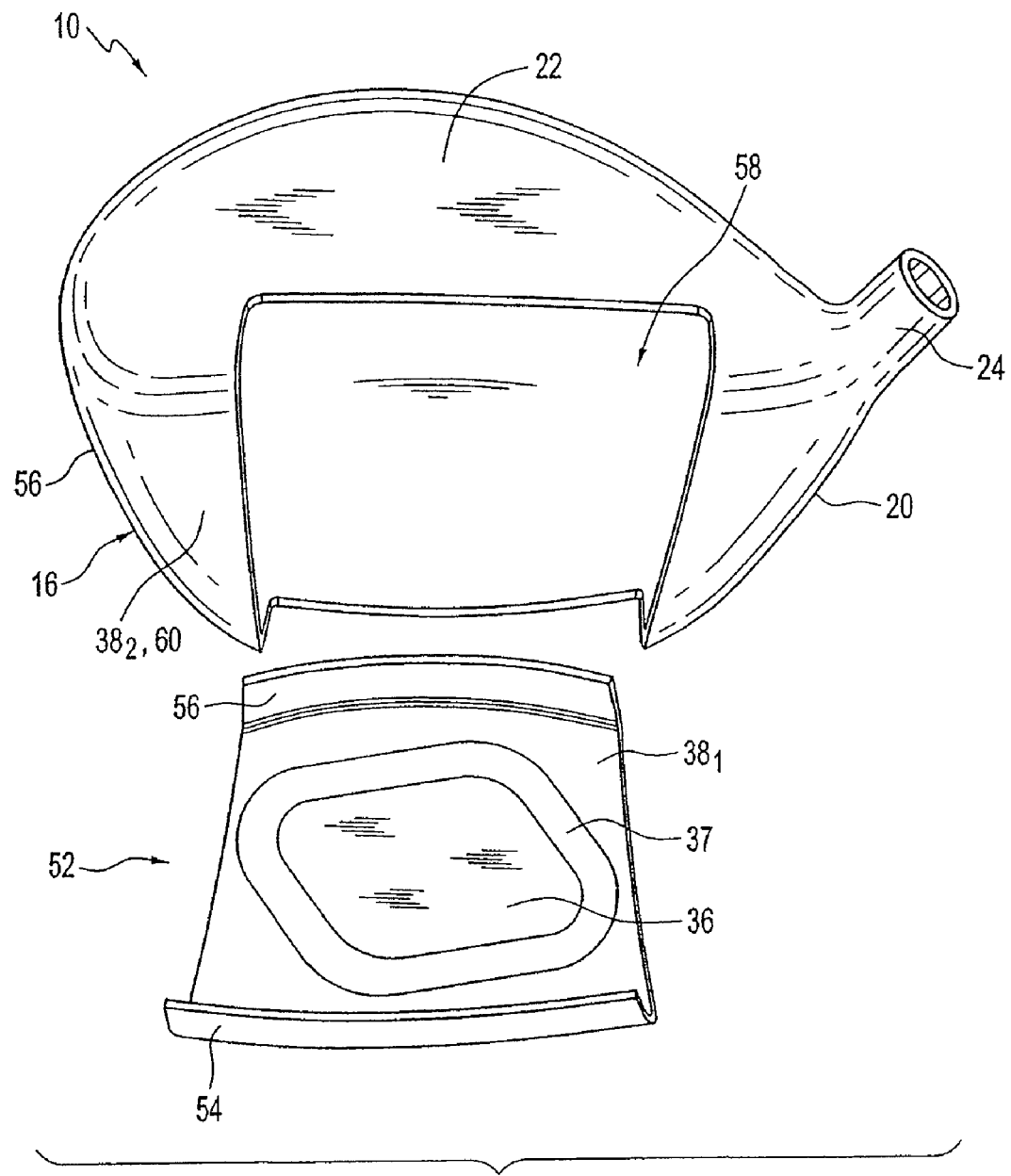
FIG. 9 is a front, exploded view of another embodiment of the present invention.

In accordance to another aspect of the invention, the face insert may include one or more side walls, wherein the side walls may form part of the crown and/or part of the sole. As shown in FIG. 9, face insert 52 comprises central zone 36, transition zone 37, a portion of intermediate zone 38, partial crown portion 54 and partial sole portion 56. Club head 10 correspondingly defines cavity 58 sized and dimensioned to receive face insert 52. Face insert 52 is preferably welded to club head 10. Face insert 52 together with face support 60 forms hitting face 16. Similar to the embodiment illustrated in FIG. 8, intermediate zone 38, designated as $38_1$ and $38_2$, can be disposed partially on face insert 52 and partially on face support 60.

EXAMPLE

Figure 10A:
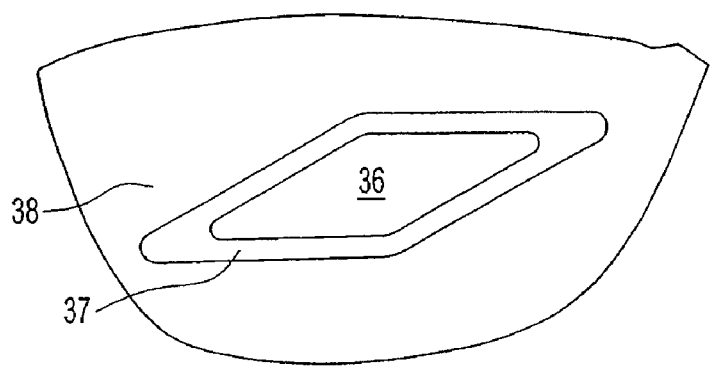
FIGS. 10(a)-10(c) illustrate the results from a comparative example, which compares iso-COR contour lines of conventional golf club head and of an embodiment of the present invention.

In this example, hitting face 16 has the following construction. The central zone 36 has a substantially parallelogram shape, as shown in FIG. 10(a), with a major axis measuring about 3 inches and a minor axis about 0.75 inches with a thickness $T_1$, of about 0.120 inch. The central zone 36 has a concentric transition zone 37 with a similar shape as the central zone 36. The intermediate zone 38 surrounds the central and transition zones with a thickness $T_2$ of 0.080 inch and comprises the remainder of the face hitting area. There is no perimeter zone 40 included in this example. The major axis of zone 36 substantially coincides with the major axis of zone 38, and these two major axes form angle theta (θ) of about 50° with the shaft axis. Furthermore, zones 36 and 37 comprise about 18% of the total face surface area. A single homogeneous material, preferably a titanium alloy, with a Young's modulus (E) of approximately $16.5 \times 10^6$ lbs/in² is used. In this example, the (FS1/FS2) ratio is 3.4 when FS1 includes both zones 36 and 37 and FS2 includes zone 38.

The test results were generated using computational techniques, which include finite element analysis models. In the computer model, the following assumptions were made: club head loft of 9°; club head mass of 195 grams; and club head material is 6AL-4V titanium alloy. The golf ball used in the model was a two-piece solid ball. Finite element models were used to predict ball launch conditions and a trajectory model was used to predict distance and landing area. The impact condition used for club coefficient of restitution (COR) tests was consistent with the USGA Rules for Golf, specifically, Rule 4-1e Appendix II Revision 2 dated Feb. 8, 1999.

Figure 10B:
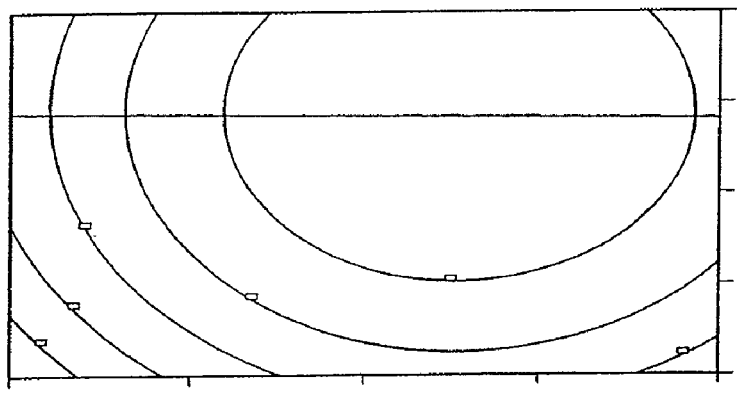
Figure 10C:
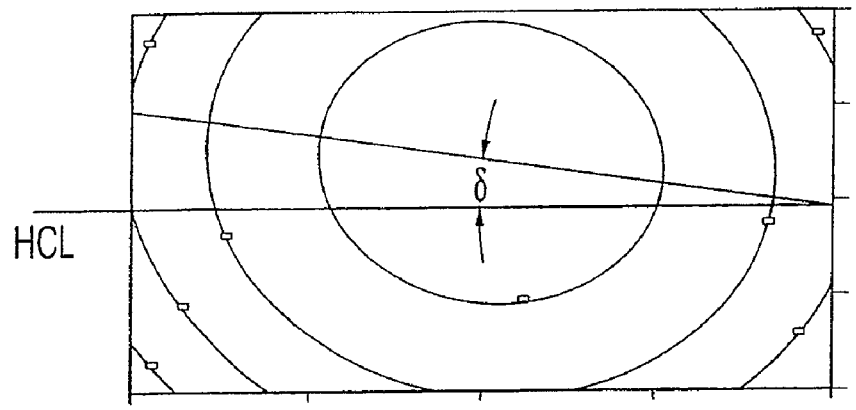

Distributions of coefficient of restitution (COR) are shown in FIGS. 10(b) and 10(c). The lines indicate contour lines, similar to the contour lines in topography maps or weather maps, and indicate lines of constant COR (hereinafter iso-COR lines). The innermost contour line indicates the highest COR region on the hitting face and outer contour lines indicate lower COR regions on the hitting face. FIG. 10(b) represents the iso-COR contours for a conventional club having a hitting face with uniform thickness, and FIG. 10(c) represents the iso-COR contours of the inventive club described in this Example.

COR or coefficient of restitution is one way of measuring ball resiliency. COR is the ratio of the velocity of separation to the velocity of approach. In this model, therefore, COR was determined using the following formula:

$$(v_{club\text{-}post} - v_{ball\text{-}post}) / (v_{ball\text{-}pre} - v_{club\text{-}pre})$$

where, $v_{club\text{-}post}$ represents the velocity of the club after impact;

$v_{ball\text{-}post}$ represents the velocity of the ball after impact;

$v_{club\text{-}pre}$ represents the velocity of the club before impact (a value of zero for USGA COR conditions); and $v_{ball\text{-}post}$ represents the velocity of the ball before impact.

COR, in general, depends on the shape and material properties of the colliding bodies. A perfectly elastic impact has a COR of one (1.0), indicating that no energy is lost, while a perfectly inelastic or perfectly plastic impact has a COR of zero (0.0), indicating that the colliding bodies did not separate after impact resulting in a maximum loss of energy. Consequently, high COR values are indicative of greater ball velocity and distance.

The iso-COR contour lines generated by the computational analysis are shown within a rectangle having dimensions of 0.5 inch by 1.0 inch, as typically used in the art. Within this rectangle, the inventive club head exhibits relatively high and substantially uniform COR values. The COR values are measured at nine points within this rectangle, i.e., the corners of the rectangle, mid-points of the sides and the geometric center of the rectangle. Additionally, the geometric center of this rectangular measurement zone preferably coincides with the geometric center of the hitting face of the club. In this example, the lowest COR within this measurement zone is 0.828 and the peak COR is 0.865. According to the present invention, the lowest COR is within 93% of the peak COR. This advantageously produces a hitting face with a substantially uniform COR and large "sweet spot."

The iso-COR contour lines of the conventional club shown in FIG. 10(b) follow a substantially elliptical pattern. Furthermore, the center of the innermost iso-COR contour line, which has the highest COR value, is offset from the geometric center of the rectangular measurement zone, indicating a reduction in COR. The major axis of these contour lines is substantially horizontal.

The iso-COR contour lines for the inventive club also follow an elliptical pattern, and as shown in FIG. 10 (c), the major axis of the pattern does not coincide with the horizontal center line, HCL, of the hitting face. The test results indicate that the major axis of the iso-COR pattern makes an angle, delta (δ), with the HCL. The angle δ is at least 5°, and more preferably at least 7° in the direction from high toe to low heel. While the major axis of central zone 36 with the highest FS runs substantially from high heel to low toe, the major axis of the iso-COR contours runs substantially in a different direction, i.e., from high toe to low heel, which advantageously coincides with the typical hit distribution that golfers make on the hitting face, discussed above. Furthermore, the center of the innermost iso-COR contour line is closer to the geometrical center of the rectangular measurement zone, indicating a higher peak COR value.

Without being limited to any particular theory, the inventors of the present invention observe that when an elliptical area of high thickness or high FS is present at or near the center of the hitting face with areas of less thickness or lower FS surrounding it, the iso-COR contour lines generally form an elliptical shape where the major axis of the iso-COR contours forms an angle with the major axis of the areas of high thickness or high FS. This arrangement of inner and intermediate zones forms a zone of relatively high flexural stiffness in the direction of high heel to low toe thereby creating high resilience in the direction of high toe to low heel. In other words, this arrangement creates a gradient of flexural stiffness in the direction of high toe to low heel and produces a desirable effect of manipulating resilience or higher coefficient of restitution (COR) in that direction. This area of improved coefficient of restitution advantageously coincides with the ball impact pattern that golfers typically make on the hitting face.

Figure 11:
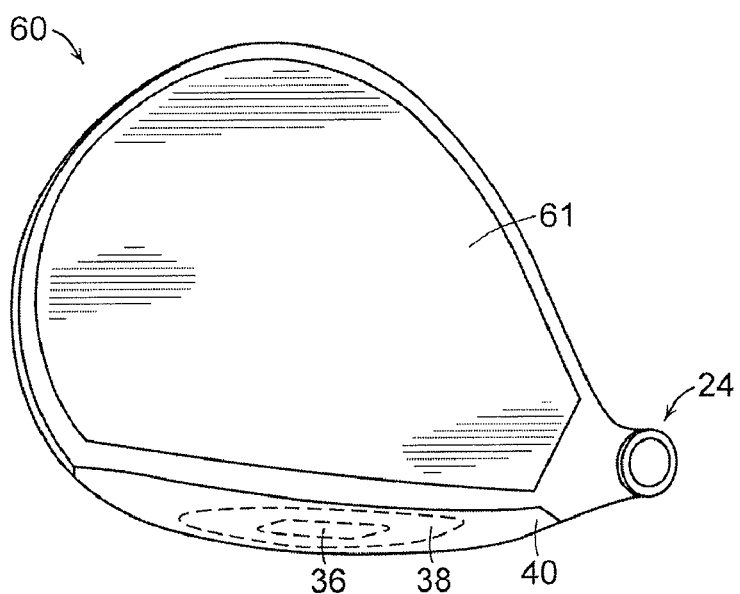
FIG. 11 is a top view of an embodiment of the invention wherein the crown is composed of a composite material.
Figure 12A:
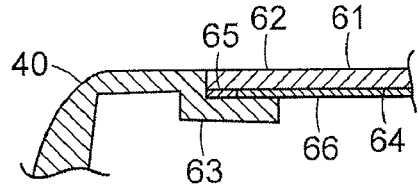
FIG. 12a is a cross-section view of the crown portion attached to the lip section of the outer portion.
Figure 12B:
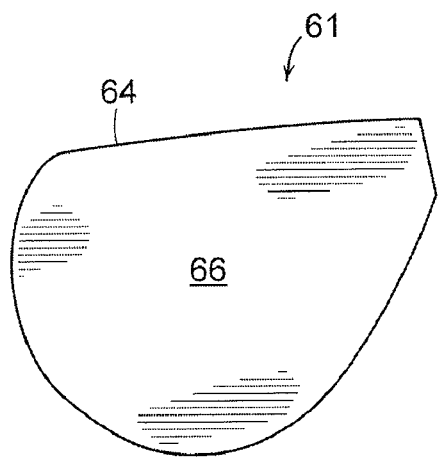
FIG. 12b is a plan view showing the layer of titanium mesh material integral with the inner surface of the crown portion.

As shown is FIG. 11, a club head embodiment of the invention is depicted having a club head 10, which includes a body portion 60, a composite crown portion 61, and a hosel 24 for attaching to a shaft (not shown). The body portion 60 comprises an outer portion 40 that includes a lip section 63, as shown in FIGS. 12a, c, e, g, h, and i. The transverse surfaces of the lip section 63 define a cutout 65. As shown in FIG. 12a, the crown portion 61 attaches to the first body portion 60 by an outer ledge section 62 being attached to the lip section 63. The outer ledge section 62 substantially forms a perimeter edge of the crown portion 61. An inventive aspect of the present invention is the inclusion of a shock absorption layer 66 integral with the inner surface 64 of the crown portion 61. For an embodiment shown in FIG. 12a, the shock absorption layer 66 covers substantially the entire inner surface 64 of the crown portion 61, as depicted by FIG. 12b. This shock absorption layer 66 is preferably composed of titanium mesh material. Although the crown portion is shown herein as only encompassing the crown of the club head 10, it is appreciated that it could also include parts of the skirt or hosel sections of the club head 10. The crown portion 61 may be cast, formed, injection molded, machined or pre-preg sheet formed.

The density range for crown portion 61 is from about 0.1 g/cc to 4.0 g/cc. Preferably the crown portion 61 may be formed from materials such as magnesium, graphite composite, a thermoplastic, but the preferred material for the crown portion 61 is graphite composite. Preferably, the crown portion 61 has a thickness in the range of about 0.1 mm to about 1.5 mm, and more preferably less than about 1.0 mm.

Figure 12C:
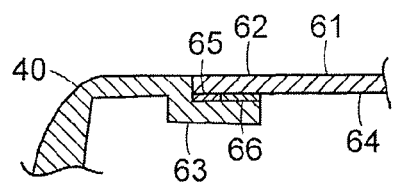
FIG. 12c is a cross-section view of another embodiment of the crown portion wherein a titanium mesh ring is integral about the perimeter edge of the crown portion.
Figure 12D:
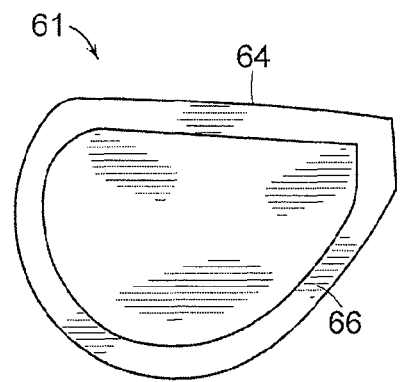
FIG. 12d is a plan view showing a ring of titanium mesh about the perimeter edge of the crown portion.

An embodiment of the invention is shown in FIGS. 12c and 12d. In this embodiment, the titanium mesh layer 66 is integral with the inner surface 64 of the crown portion 61 is in the shape of a ring, such that it is juxtaposed the outer ledge 62 and the lip section 63.

Figure 12E:
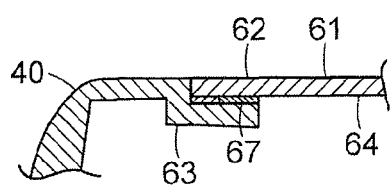
FIG. 12e is a cross-section view of an embodiment of the invention wherein a gasket is disposed between the lip section of the outer portion and the crown portion.
Figure 12F:
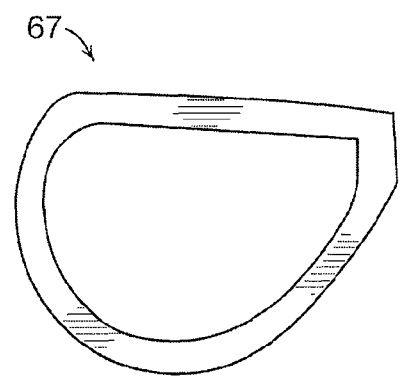
FIG. 12f is a plan view of the gasket of FIG. 12e.

Another embodiment of the invention is described on FIGS. 12e and 12f, wherein, the shock absorption material is a separate gasket 67, and is disposed between the outer ledge section 62 and the lip section 63. Other materials, such as a viscoelastic material or an aluminum foil, may be substituted in lieu of the titanium gasket.

Another way to dampen vibrations according to the invention is shown in FIG. 12g, wherein a gap 68 is created between the transverse surfaces of the body portion 60 and the crown portion 61. In FIG. 12g, this gap 68 has a substantially rectangular shape, while in FIG. 12h, an L-shaped gap 69, creates the bond between the transverse surfaces. However, both are preferably filled with a shock absorbing material such as putty or a rubber based structural adhesive, such as those provided by PPG Industries, Inc. under the trade name CORABOND®HC7707.

The materials for forming the body portion 60 may be stainless steel, pure titanium or a titanium alloy. The more preferred material comprises titanium alloys, such as titanium 6-4 alloy, which comprises 6% aluminum and 4% vanadium. The body portion 60 may be manufactured through casting with a face insert, or formed portions with a face insert. The face insert is made by casting, machining sheet metal or forming sheet metal. Another embodiment can be created by forming a wrapped face, from forging, stamping, powdered metal forming, or metal-injection molding.

Tests were conducted on each of two golf clubs of the present invention. The only physical difference between the two clubs was that one of the clubs was manufactured with the shock absorption layer 66, as shown in FIGS. 12a and 12b, and the other club was made without any such shock absorption layer. Identical shaft specifications were used for both test clubs, and the ball was a Pinnacle Gold, as manufactured by Titleist®. Test data taken over a frequency range of 3,000 to 12,000 Hz indicated swing speed is a variable in the percentage of dampening that was achieved. At a swing speed of 90 mph, the noise was dampened between a range of about 28% to 50% over a frequency range of about 3800 Hz to 10,000 Hz, while at a swing speed of 105 mph the noise was dampened about 20% to 32% over the same Hz range.

An embodiment of the invention provides an improvement in the percentage of club area relative to the head volume. With the composite crown portion 61 being considerably lighter than titanium, weight is removed from the crown and may then be redistributed into weight inserts in the body and face. The weight relocation helps to position the center of gravity lower. As seen in FIG. 13, an embodiment of the present invention provides a club head with the center of gravity located between 50 to 55% of the face height with a face area greater than 50 cm$^2$. The combination of shaft characteristics with the present invention provides for dynamic results. The shaft used in the embodiment is a lightweight rayon Model SL-45, as manufactured by Mitsubishi. It has a weight that is less than 50 grams and preferably less than 48 grams. The shaft torque is greater than about 3.5° and preferably greater than about 4°. The shaft tip stiffness is less than 900 cpm and greater than 600 cpm as measured 320 mm from the tip. The face is closed at an angle greater than 1°, preferably 2°, and the face has an effective hitting area greater than 7.0 in$^2$ and preferably greater than 7.25 in$^2$. Combining this center of gravity location with the ultra-light shaft design and low tip stiffness, a high right to left trajectory is promoted with increased swing speed. The lower center of gravity promotes a high launch, a larger head size yields a higher moment of inertia, and the larger face area allows for more forgiveness.

As suggested above, FIG. 13 shows the position of the center of gravity as it relates to face height for the King Cobra 454 COMP driver as manufactured by The Acushnet Company and depicts a face area of 48.4 cm$^2$, overall club weight of 290 (with a Mitsubishi Rayon SL-45 shaft having a weight of 45 grams, and a length of 45.5"). The magnitude of the effective hitting area of the King Cobra 454 COMP golf club is shown in FIGS. 14a and 14b. The effective hitting area of the King Cobra 454 is about 7.5 in$^2$ versus an effective hitting area of about 5.0 in² for an ERC Fusion golf club, as manufactured by the Callaway Golf Company of Carlsbad, Calif.

A significant performance criteria in the design of a golf club is the club's "forgiveness" or its ability to provide near optimum hitting for golf hits that are not struck right on the perfect "sweet spot" of the club. The "sweet spot" of a golf club is usually referred to as that spot on the club face wherein maximum Coefficient of Restitution is obtained. The golf club of the present invention provides a "sweet zone" or nine (9) points across the club face, in which the club will deliver near maximum COR, at not just one particular point on the club face, but at any point within the sweet zone.

FIGS. 14a and 14b make a 9 point comparison of the club faces of a model 454 Cobra versus the ERC Fusion club of Callaway Golf Company. The spin of the golf ball coming off the club face is an important parameter and in a perfect situation, the spin would be the same for the entire club face. In the design of a club face, having a minimum variance of spin across a large area of the face is a highly desired performance characteristic. The performance data shown on FIGS. 14a and 14b are based on striking the golf ball at an 11° launch angle and a club speed of 90 mph. The spin imparted to the ball coming off the King Cobra 454 face is much higher across the entire face (average spin of 2375 rpm) than that of the ERC Fusion club (average spin of 2070 rpm), the variance across the "sweet zone" of the King Cobra 454 club is only 475 rpm to 850 rpm for the ERC Fusion club. This demonstrates a club face that will consistently yield shots more consistent over a greater surface area.

While various descriptions of the present invention are described above, it should be understood that the various features of each embodiment can be used alone or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, the face and/or individual zones can have thickness variations in a step-wise or continuous fashion. Other modifications include a perimeter zone that has a thickness that is greater than or less than the adjacent, intermediate zone. In addition, the shapes of the central, intermediate, and perimeter zones are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:

1. A golf club head comprising:
   a face portion including an inner zone and an intermediate zone surrounding said inner zone, said inner zone having a relatively high flexural stiffness compared to said intermediate zone; and
   a body portion connected to said face portion,
   wherein said inner zone has a generally elliptical shape with a major axis and a minor axis wherein said major axis aligns substantially in a direction of high heel to low toe,
   wherein said face portion contains a sweet zone encompassing said inner zone and said intermediate zone, and
   wherein no point within said sweet zone may have a COR that is 93% less than a maximum COR.

2. The golf club head of claim 1, wherein said sweet zone encompasses only said inner zone and said intermediate zone.

3. The golf club head of claim 2, wherein said intermediate zone is concentric with said inner zone.

4. The golf club head of claim 3, wherein said inner zone and said intermediate zone creates a gradient of flexural stiffness in said direction of high toe to low heel.

5. The golf club head of claim 4, wherein said inner zone contains a geometric center that approximately coincides with a geometric center of said face portion.

6. The golf club head of claim 5, wherein said high flexural stiffness of said inner zone is greater than approximately twice said flexural stiffness of said intermediate zone.

7. The golf club head of claim 4, wherein said sweet zone encompassing said inner zone and said intermediate zone encompasses approximately 15% to approximately 60% of said face portion.

8. The golf club head of claim 4, further comprising a shaft having a shaft axis concentric said shaft, wherein said inner zone and said intermediate zone are non-circular, and wherein said minor axis is oriented orthogonal to said major axis such that said major axis forms an angle of between 10 degrees and 60 degrees with said shaft axis.

9. The golf club head of claim 8, wherein said angle is between 20 degrees and 50 degrees.

10. The golf club head of claim 9, wherein said angle is between 25 degrees and 45 degrees.

11. A golf club head comprising:
    a face portion including an inner zone and an intermediate zone surrounding said inner zone, said inner zone having a relatively high flexural stiffness such that a measurement zone, defined by a perimeter of said intermediate zone with a geometric center that coincides with a geometric center of said face portion, has a lowest COR that is at least 93 percent of maximum COR;
    a body portion formed of a material having a first density;
    a crown portion formed of a second material having a second density that is less than said first density, such that said club head has a center of gravity that is located below a horizontal plane containing said geometric center of said face portion; and
    a dampening layer juxtaposed between said body portion and said crown portion for acoustical attenuation between a frequencies of 3800 Hz and 10,000 Hz.

12. The golf club head of claim 11, wherein no point within said measurement zone may have a COR that is 93% less than a maximum COR.

13. The golf club head of claim 12, wherein said inner zone has a generally elliptical shape, with a major axis that aligns substantially in a direction of high heel to low toe.

14. The golf club head of claim 13, wherein said inner zone and said intermediate zone encompasses approximately 15% to approximately 60% of said face portion.

15. The golf club head of claim 14, further comprising a shaft having a shaft axis concentric said shaft, wherein said inner zone and said intermediate zone are non-circular containing a major axis and a minor axis, and wherein said minor axis is oriented orthogonal to said major axis such that said major axis forms an angle of between 10 degrees ad 60 degrees with said shaft axis.

16. The golf club head of claim 15, wherein said angle is between 20 degrees and 50 degrees.

17. The golf club head of claim 16, wherein said angle is between 25 degrees and 45 degrees.

18. A golf club head comprising:
    a face portion including an inner zone and an intermediate zone surrounding said inner zone, said inner zone having a relatively high flexural stiffness compared to said intermediate zone;

a body portion connected to said face portion, and a shaft having a shaft axis concentric said shaft;

wherein said face portion contains a sweet zone encompassing said inner zone and said intermediate zone, wherein said sweet zone encompasses approximately 15% to approximately 60% of said face portion, wherein no point within said sweet zone may have a COR that is 93% less than a maximum COR wherein said inner zone and said intermediate zone are non-circular, and wherein said minor axis is oriented orthogonal to said major axis such that said major axis forms an angle of between 10 degrees and 60 degrees with said shaft axis.

19. The golf club head of claim 18, wherein said body portion further comprises: a crown portion formed of a second material having a second density that is less than said first density, such that said club head has a center of located below a horizontal plane containing a geometric center of said face portion; and a dampening layer juxtaposed between said body portion and said crown portion for acoustical attenuation between a frequencies of 3800 Hz and 10,000 Hz.

20. The golf club head of claim 19, wherein said inner zone contains a geometric center that approximately coincides with said geometric center of said face portion.

* * * * *